US010196608B2

(12) United States Patent
Poirot et al.

(10) Patent No.: US 10,196,608 B2
(45) Date of Patent: Feb. 5, 2019

(54) METHOD FOR IN SITU INHIBITION OF REGULATORY T CELLS

(71) Applicant: CELLECTIS, Paris (FR)

(72) Inventors: Laurent Poirot, Paris (FR); Philippe Duchateau, Draveil (FR)

(73) Assignee: CELLECTIS, Paris (FR)

(*) Notice: Subject to any disclaimer, the term of this patent is extended or adjusted under 35 U.S.C. 154(b) by 0 days.

(21) Appl. No.: 15/120,060

(22) PCT Filed: Feb. 20, 2015

(86) PCT No.: PCT/EP2015/053592
§ 371 (c)(1),
(2) Date: Aug. 18, 2016

(87) PCT Pub. No.: WO2015/124715
PCT Pub. Date: Aug. 27, 2015

(65) Prior Publication Data
US 2017/0067022 A1 Mar. 9, 2017

(30) Foreign Application Priority Data
Feb. 21, 2014 (DK) .................................. 201470088

(51) Int. Cl.
| C12N 9/16 | (2006.01) |
| A61K 35/17 | (2015.01) |
| C07K 14/47 | (2006.01) |
| C07K 16/28 | (2006.01) |
| C07K 14/715 | (2006.01) |
| C07K 14/725 | (2006.01) |
| C12N 5/0783 | (2010.01) |

(52) U.S. Cl.
CPC ............ *C12N 5/0638* (2013.01); *A61K 35/17* (2013.01); *C07K 14/4703* (2013.01); *C07K 14/7051* (2013.01); *C07K 14/7155* (2013.01); *C07K 16/2803* (2013.01); *C07K 16/2866* (2013.01); *C12N 5/0636* (2013.01); *C12N 9/16* (2013.01); *C07K 2317/622* (2013.01); *C07K 2319/74* (2013.01); *C12N 2501/60* (2013.01); *C12N 2510/00* (2013.01)

(58) Field of Classification Search
None
See application file for complete search history.

(56) References Cited

U.S. PATENT DOCUMENTS

2010/0267623 A1* 10/2010 Casares Lagar ........ C07K 7/08
514/2.4
2011/0158957 A1* 6/2011 Bonini .................... C12N 9/22
424/93.7
2014/0134142 A1* 5/2014 Smith .................... A61K 35/17
424/93.21
2014/0322212 A1* 10/2014 Brogdon .......... C07K 14/70517
424/134.1
2016/0145337 A1* 5/2016 Galetto ................ A61K 35/17
424/93.21

FOREIGN PATENT DOCUMENTS

WO  WO 2012/079000 A1   6/2012
WO  WO 2013/123061 A1 * 8/2013 ............. C07K 14/46

OTHER PUBLICATIONS

Benedict et al. (J. Exp. Medicine, 2001, 193(1) 89-99).*
Jiang et al. (J. Biol. Chem. 2003, 278(7) 4763-4769).*
Almagro & Fransson, Frontiers in Bioscience 2008; 13:1619-33 (Year: 2008).*
Casares et al., "A Peptide Inhibitor of FOXP3 Impairs Regulatory T Cell Activity and Improves Vaccine Efficacy in Mice," The Journal of Immunology, vol. 185, 2010, pp. 5150-5159.
Dasgupta et al., "Regulatory T cells: A review," The National Medical Journal of India, vol. 25, 2012, pp. 341-351.
Fransson et al., "CAR/FoxP3-engineered T regulatory cells target the CNS and suppress EAE upon intranasal delivery," Journal of Neuroinflammation, vol. 9, 2012, pp. 1-12.
International Search Report issued in International Patent Application No. PCT/EP2015/053592 dated Apr. 29, 2015.
Lee et al., "In vivo inhibition of Human CD19-Targeted Effector T Cells by Natural T Regulatory Cells in Xenotransplant Murine Model of B Cell Malignancy," Cancer Res, vol. 71, Apr. 2011, pp. 2871-2881.
Loskog et al., "Addition of the CD28 signaling domain to chimeric T-cell receptors enhances chimeric T-cell resistance to T regulatory cells," Leukemia, vol. 20, 2006, pp. 1819-1828.
Pegram et al., "Tumor-targeted T cells modified to secret IL-12 eradicate systemic tumors without need for prior condition," Blood, vol. 119, May 2012, pp. 4133-4141.
Jena B. et al., "Redirecting T-cell specificity by introducing a tumor-specific chimeric antigen receptor" Blood, vol. 116, No. 7, 2010, pp. 1035-1044.

* cited by examiner

*Primary Examiner* — Peter J Reddig
(74) *Attorney, Agent, or Firm* — Arrigo, Lee, Guttmann & Mouta-Bellum LLP

(57) ABSTRACT

The present invention pertains to engineered T-cells, method for their preparation and their use as medicament, particularly for immunotherapy. The engineered T-cells of the invention are designed to express both a Chimeric Antigen Receptor (CAR) directed against at least one antigen expressed at the surface of a malignant or infected cell, and a secreted inhibitor of regulatory T-cells (Treg). Preferably, such secreted inhibitor is a peptide inhibitor of forkhead/winged helix transcription factor 3 (FoxP3), a specific factor involved into the differentiation of T-cells into regulatory T-cells. The engineered T-cells of the invention direct their immune activity towards specific malignant or infected cells, while at the same time will prevent neighboring regulatory T-cells from modulating the immune response. The invention opens the way to standard and affordable adoptive immunotherapy strategies, especially for treating or preventing cancer, and bacterial or viral infections.

16 Claims, 6 Drawing Sheets
Specification includes a Sequence Listing.

SEQUENCE LISTING

<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: peptide inhibitor of FoxP3

<400> SEQUENCE: 1

Arg Asp Phe Gln Ser Phe Arg Lys Met Trp Pro Phe Phe Ala Met
1               5                   10                  15

<210> SEQ ID NO 2
<211> LENGTH: 45
<212> TYPE: DNA
<213> ORGANISM: Artificial Sequence
<220> FEATURE:
<223> OTHER INFORMATION: peptide inhibitor of FoxP3

<400> SEQUENCE: 2
cgcgactttc aaagtttccg taagatgtgg ccgttttttg caatg                45

<210> SEQ ID NO 3
<211> LENGTH: 16
<212> TYPE: PRT
<213> ORGANISM: Artificial Sequence
<220> FEATURE:
<223> OTHER INFORMATION: peptide inhibitor of FoxP3

<400> SEQUENCE: 3

Met Arg Asp Phe Gln Ser Phe Arg Lys Met Trp Pro Phe Phe Ala Met
1               5                   10                  15

<210> SEQ ID NO 4
<211> LENGTH: 48
<212> TYPE: DNA
<213> ORGANISM: Artificial Sequence
<220> FEATURE:
<223> OTHER INFORMATION: peptide inhibitor of FoxP3

<400> SEQUENCE: 4
atgcgcgact tcaaagttt ccgtaagatg tggccgtttt ttgcaatg               48

<210> SEQ ID NO 5
<211> LENGTH: 495
<212> TYPE: PRT
<213> ORGANISM: Artificial sequence
<220> FEATURE:
<223> OTHER INFORMATION: anti-CD19 CAR

<400> SEQUENCE: 5

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly
    130                 135                 140

Gly Ser Gly Gly Gly Ser Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 6
<211> LENGTH: 848
<212> TYPE: PRT
<213> ORGANISM: Artificial sequence
<220> FEATURE:
<223> OTHER INFORMATION: Multi-chain CAR

<400> SEQUENCE: 6

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
                35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
            115                 120                 125

Gly Ser Arg Val Phe Asp Tyr Trp Gly Gln Gly Thr Thr Leu Thr Val
        130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Arg Ala Glu Gly Arg Gly Ser Leu Leu Thr Cys
370                 375                 380

Gly Asp Val Glu Glu Asn Pro Gly Pro Met Asp Thr Glu Ser Asn Arg
385                 390                 395                 400

Arg Ala Asn Leu Ala Leu Pro Gln Glu Pro Ser Ser Val Pro Ala Phe
            405                 410                 415

Glu Val Leu Glu Ile Ser Pro Gln Glu Val Ser Ser Gly Arg Leu Leu
```

-continued

```
                420             425             430
Lys Ser Ala Ser Ser Pro Leu His Thr Trp Leu Thr Val Leu Lys
            435             440             445
Lys Glu Gln Glu Phe Leu Gly Val Thr Gln Ile Leu Thr Ala Met Ile
450             455             460
Cys Leu Cys Phe Gly Thr Val Val Cys Ser Val Leu Asp Ile Ser His
465             470             475             480
Ile Glu Gly Asp Ile Phe Ser Ser Phe Lys Ala Gly Tyr Pro Phe Trp
                485             490             495
Gly Ala Ile Phe Phe Ser Ile Ser Gly Met Leu Ser Ile Ile Ser Glu
            500             505             510
Arg Arg Asn Ala Thr Tyr Leu Val Arg Gly Ser Leu Gly Ala Asn Thr
            515             520             525
Ala Ser Ser Ile Ala Gly Gly Thr Gly Ile Thr Ile Leu Ile Ile Asn
            530             535             540
Leu Lys Lys Ser Leu Ala Tyr Ile His Ile His Ser Cys Gln Lys Phe
545             550             555             560
Phe Glu Thr Lys Cys Phe Met Ala Ser Phe Ser Thr Glu Ile Val Val
                565             570             575
Met Met Leu Phe Leu Thr Ile Leu Gly Leu Gly Ser Ala Val Ser Leu
            580             585             590
Thr Ile Cys Gly Ala Gly Glu Glu Leu Lys Gly Asn Lys Val Pro Glu
            595             600             605
Lys Arg Gly Arg Lys Lys Leu Leu Tyr Ile Phe Lys Gln Pro Phe Met
            610             615             620
Arg Pro Val Gln Thr Thr Gln Glu Asp Gly Cys Ser Cys Arg Phe
625             630             635             640
Pro Glu Glu Glu Gly Gly Cys Glu Leu Gly Ser Gly Val Lys Gln
                645             650             655
Thr Leu Asn Phe Asp Leu Leu Lys Leu Ala Gly Asp Val Glu Ser Asn
            660             665             670
Pro Gly Pro Met Ile Pro Ala Val Val Leu Leu Leu Leu Leu Val
            675             680             685
Glu Gln Ala Ala Ala Leu Gly Glu Pro Gln Leu Cys Tyr Ile Leu Asp
            690             695             700
Ala Ile Leu Phe Leu Tyr Gly Ile Val Leu Thr Leu Leu Tyr Cys Arg
705             710             715             720
Leu Lys Ile Gln Val Arg Lys Ala Ala Ile Thr Ser Tyr Glu Lys Ser
                725             730             735
Arg Val Lys Phe Ser Arg Ser Ala Asp Ala Pro Ala Tyr Gln Gln Gly
            740             745             750
Gln Asn Gln Leu Tyr Asn Glu Leu Asn Leu Gly Arg Arg Glu Glu Tyr
            755             760             765
Asp Val Leu Asp Lys Arg Arg Gly Arg Asp Pro Glu Met Gly Gly Lys
            770             775             780
Pro Arg Arg Lys Asn Pro Gln Glu Gly Leu Tyr Asn Glu Leu Gln Lys
785             790             795             800
Asp Lys Met Ala Glu Ala Tyr Ser Glu Ile Gly Met Lys Gly Glu Arg
                805             810             815
Arg Arg Gly Lys Gly His Asp Gly Leu Tyr Gln Gly Leu Ser Thr Ala
            820             825             830
Thr Lys Asp Thr Tyr Asp Ala Leu His Met Gln Ala Leu Pro Pro Arg
            835             840             845
```

<210> SEQ ID NO 7
<211> LENGTH: 2547
<212> TYPE: DNA
<213> ORGANISM: Artificial Sequence
<220> FEATURE:
<223> OTHER INFORMATION: Multi-chain CAR

<400> SEQUENCE: 7

```
atggctcctg ccatggaatc ccctactcta ctgtgtgtag ccttactgtt cttcgctcca      60
gatggcgtgt tagcagaggt gcagttgcag cagtcagggc cagagttgat taagcccgga     120
gcctccgtca gatgtcctg caaggccagc gggtacactt tcaccagcta cgtcatgcat     180
tgggtgaagc agaagccagg ccagggctt gagtggattg gtacatcaa ccctacaac     240
gacgggacca atacaacga gaaattcaag ggcaaagcca cactcacctc cgataagtcc     300
tcctctaccg cctacatgga gctcagctcc ctgacctccg aggatagcgc tgtgtattac     360
tgcgcaaggg gcacatacta ctatggctct agggtgttcg actactgggg cagggcact     420
actctcacag tgagctcagg cggaggaggc agtggcggag ggggaagtgg gggcggcggc     480
agcgatattg tcatgaccca ggcagcccct agtatccctg tgactccagg cgagagcgtg     540
agcatcagct gccggtccag caagagcctg ctgaacagta acggaaacac ataccctctac     600
tggtttctgc agaggcccgg ccagagccct cagctgctga tttaccgcat gtcaaatctt     660
gcctctgggg tgcccgatag atttagtggg agcggatccg gcacagcttt tacattgcgg     720
atctccagag tcgaggccga agacgtgggg gtctattact gtatgcaaca cctggaatac     780
cccttacct tcggagccgg cacaaagctg gagctgaagc gggctgacac cacaacccc     840
gctccaaggc ccctacccc cgcaccaact attgcctccc agccactctc actgcggcct     900
gaggcctgtc ggcccgctgc tggaggcgca gtgcatacaa ggggcctcga tttcgcctgc     960
gatttttta tcccattgtt ggtggtgatt ctgtttgctg tggacacagg attattatc    1020
tcaactcagc agcaggtcac atttctcttg aagattaaga gaaccaggaa aggcttcaga    1080
cttctgaacc cacatcctaa gccaaacccc aaaaacaaca gagccgaggg cagaggcagc    1140
ctgctgacct gcggcgacgt ggaggagaac ccaggcccca tggacacaga aagtaatagg    1200
agagcaaatc ttgctctccc acaggagcct tccagtgtgc ctgcatttga agtcttggaa    1260
atatctcccc aggaagtatc ttcaggcaga ctattgaagt cggcctcatc cccaccactg    1320
catacatggc tgacagtttt gaaaaagag caggagttcc tgggggtaac acaaattctg    1380
actgctatga tatgcctttg ttttggaaca gttgtctgct ctgtacttga tatttcacac    1440
attgagggag acatttttttc atcatttaaa gcaggttatc cattctgggg agccatattt    1500
ttttctattt ctggaatgtt gtcaattata tctgaaagga gaaatgcaac atatctggtg    1560
agaggaagcc tggagcaaaa cactgccagc agcatagctg ggggaacggg aattaccatc    1620
ctgatcatca acctgaagaa gagcttggcc tatatccaca tccacagttg ccagaaattt    1680
tttgagacca agtgctttat ggcttccttt tccactgaaa ttgtagtgat gatgctgttt    1740
ctcaccattc tgggacttgg tagtgctgtg tcactcacaa tctgtggagc tggggaagaa    1800
ctcaaaggaa acaaggttcc agagaaacg ggccggaaga agctcctcta catttttaag    1860
cagcctttca tgcggccagt gcagacaacc aagaggagg atgggtgttc ctgcagattc    1920
cctgaggaag aggaaggcgg gtgcgagctg ggttctggcg tgaaacgac tttgaatttt    1980
gaccttctca agttggcggg agacgtggag tccaacccag ggcccatgat tccagcagtg    2040
```

```
gtcttgctct tactccttt tggttgaacaa gcagcggccc tgggagagcc tcagctctgc    2100
tatatcctgg atgccatcct gtttctgtat ggaattgtcc tcaccctcct ctactgtcga    2160
ctgaagatcc aagtgcgaaa ggcagctata accagctatg agaaatcaag agtgaagttc    2220
tccaggagcg cagatgcccc cgcctatcaa cagggccaga accagctcta caacgagctt    2280
aacctcggga ggcgcgaaga atacgacgtg ttggataaga aaggggggcg ggaccccgag    2340
atgggaggaa agccccggag gaagaaccct caggagggcc tgtacaacga gctgcagaag    2400
gataagatgg ccgaggccta ctcagagatc gggatgaagg gggagcggcg ccgcgggaag    2460
gggcacgatg gcctctacca ggggctgagc acagccacaa aggacacata cgacgccttg    2520
cacatgcagg cccttccacc ccggtga                                        2547
```

<210> SEQ ID NO 8
<211> LENGTH: 251
<212> TYPE: PRT
<213> ORGANISM: Artificial Sequence
<220> FEATURE:
<223> OTHER INFORMATION: Anti-CD19 CAR

<400> SEQUENCE: 8

```
Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Gly Gly Gly Gly Ser Gly Gly
        115                 120                 125

Gly Gly Ser Gly Gly Gly Gly Ser Asp Ile Val Met Thr Gln Ala Ala
    130                 135                 140

Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Tyr Pro Phe Thr Phe Gly
225                 230                 235                 240

Ala Gly Thr Lys Leu Glu Leu Lys Arg Ala Asp
                245                 250
```

<210> SEQ ID NO 9
<211> LENGTH: 15

```
<212> TYPE: PRT
<213> ORGANISM: Artificial Sequence
<220> FEATURE:
<223> OTHER INFORMATION: scrambled p60

<400> SEQUENCE: 9

Met Lys Met Phe Phe Asp Ala Phe Pro Gln Arg Arg Ser Trp Phe
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

Gly Ser Ser Ser Ser
1               5

<210> SEQ ID NO 11
<211> LENGTH: 18
<212> TYPE: PRT
<213> ORGANISM: Gallus gallus

<400> SEQUENCE: 11

Met Arg Ser Leu Leu Ile Leu Val Leu Cys Phe Leu Pro Leu Ala Ala
1               5                   10                  15

Leu Gly

<210> SEQ ID NO 12
<211> LENGTH: 20
<212> TYPE: PRT
<213> ORGANISM: Artificial Sequence
<220> FEATURE:
<223> OTHER INFORMATION: 3R CLSP

<400> SEQUENCE: 12

Met Arg Arg Arg Ser Leu Leu Ile Leu Val Leu Cys Phe Leu Pro Leu
1               5                   10                  15

Ala Ala Leu Gly
            20

<210> SEQ ID NO 13
<211> LENGTH: 21
<212> TYPE: PRT
<213> ORGANISM: Artificial Sequence
<220> FEATURE:
<223> OTHER INFORMATION: 4R CLSP

<400> SEQUENCE: 13

Met Arg Arg Arg Arg Ser Leu Leu Ile Leu Val Leu Cys Phe Leu Pro
1               5                   10                  15

Leu Ala Ala Leu Gly
            20

<210> SEQ ID NO 14
<211> LENGTH: 18
<212> TYPE: PRT
<213> ORGANISM: Homo sapiens

<400> SEQUENCE: 14

Met Lys Ala Leu Ile Val Leu Gly Leu Val Leu Leu Ser Val Thr Val
1               5                   10                  15
```

-continued

```
Gln Gly

<210> SEQ ID NO 15
<211> LENGTH: 20
<212> TYPE: PRT
<213> ORGANISM: Homo sapiens

<400> SEQUENCE: 15

Met Tyr Arg Met Gln Leu Leu Ser Cys Ile Ala Leu Ser Leu Ala Leu
1               5                   10                  15

Val Thr Asn Ser
            20

<210> SEQ ID NO 16
<211> LENGTH: 20
<212> TYPE: PRT
<213> ORGANISM: Artificial Sequence
<220> FEATURE:
<223> OTHER INFORMATION: 3K HLSP

<400> SEQUENCE: 16

Met Lys Lys Lys Ala Leu Ile Val Leu Gly Leu Val Leu Leu Ser Val
1               5                   10                  15

Thr Val Gln Gly
            20

<210> SEQ ID NO 17
<211> LENGTH: 22
<212> TYPE: PRT
<213> ORGANISM: Artificial Sequence
<220> FEATURE:
<223> OTHER INFORMATION: 3R IL2SP

<400> SEQUENCE: 17

Met Tyr Arg Arg Arg Met Gln Leu Leu Ser Cys Ile Ala Leu Ser Leu
1               5                   10                  15

Ala Leu Val Thr Asn Ser
            20
```

METHOD FOR IN SITU INHIBITION OF REGULATORY T CELLS

CROSS REFERENCE TO RELATED APPLICATION

This application is a 35 U.S.C. 371 National Phase of PCT Application No. PCT/EP2015/053592 filed Feb. 20, 2015 which claims priority to Danish Patent Application No. PA201470088 filed Feb. 21, 2014, the disclosure of these prior applications are hereby incorporated in their entirety by reference.

FIELD OF THE INVENTION

The present invention pertains to engineered T-cells, method for their preparation and their use as medicament, particularly for immunotherapy. The engineered T-cells of the invention are designed to express locally a secreted inhibitor of regulatory T-cells (Treg). Preferably, such secreted inhibitor is a peptide inhibitor of forkhead/winged helix transcription factor 3 (FoxP3), a specific factor involved into the differentiation of T-cells into regulatory T-cells. Said T-cells are preferably endowed with Chimeric Antigen Receptors (CAR) directed against at least one antigen expressed at the surface of a malignant or infected cell. The engineered T-cells of the invention thereby direct their immune activity towards specific malignant or infected cells, while at the same time prevent neighbouring regulatory T-cells from modulating the immune response. The invention opens the way to standard and affordable adoptive immunotherapy strategies, especially for treating or preventing cancer, and bacterial or viral infections.

BACKGROUND OF THE INVENTION

Cellular adaptive immunity is mediated by T-lymphocytes, also known as T-cells, which upon recognition of a non-self or tumoral antigen can either destroy the target cell or orchestrate an immune response with other cells of the immune system.

Adoptive immunotherapy, which involves the transfer of autologous antigen-specific T-cells generated ex vivo, is a promising strategy to treat viral infections and cancer. The T-cells used for adoptive immunotherapy can be generated either by expansion of antigen-specific T-cells or redirection of T-cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T-cells has been shown to be successful in treating melanoma.

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

While cytotoxic T-lymphocyte (CTL; also known as cytotoxic T-cells) and T helper cells play a central role in the cellular immune response, regulatory T-cells (Tregs), formerly known as suppressor T-cells, modulate or suppress immune responses, particularly to prevent autoimmunity and maintain tolerance to self-antigen. Because of their immune regulatory function, the presence of regulatory T-cells at a cancer or infection site may hinder the induction of an immune response against cancer or infectious pathogens (Aandahl E. M. et al. (2004); Cabrera R. et al. (2004); Viguier M. et al. (2004); Woo E. Y. et al (2001)). Therefore, in certain pathogenic situations such as chronic infectious diseases or cancer it may be desirable to suppress the activity of regulatory T-cells to allow a more potent immune response to occur. On another hand, vaccine strategies were developed based on the finding that vaccine efficacy could be improved by reducing the activity of regulatory T-cells, for instance by controlling the activity of the forkhead/winged helix transcription factor 3 (FoxP3). In particular, a peptide inhibitor of FOXP3, called P60, was found to improve vaccine efficacy in mice (Casares et al., 2010).

Dysfunction of FOXP3 is however associated with serious autoimmune disorders such as systemic lupus erythematosus or X-lined IPEX syndrome, such that systemic administration of inhibitors directed against, e.g, FoxP3, is currently not deemed a suitable option in immune therapy. The release of such inhibitors in the blood stream or even locally may lead to toxic effects by unleashing autoimmune reactions in organs not affected by the primary disease.

Accordingly, new therapeutic strategies are needed to facilitate an effective immune response while reducing possible toxic side effects in non-affected areas of the body. This need is addressed by the present invention by providing specific in-situ inhibition of regulatory T-cells as part of a CAR immunotherapy.

SUMMARY OF THE INVENTION

The present invention concerns methods for preparing engineered T-cells able to neutralize the activity of regulatory T-cells in the close environment of pathological cells by heterologous expression of a factor inhibiting the activity of said regulatory T-cells.

According to one aspect of the invention, the method can be more particularly applied to tumor-infiltrating lymphocytes (TIL), which are T-cells expressing endogenous antigen receptor specific for tumor cells (i.e. upon natural clonal selection within the patient). According to this aspect of the invention, the cells are relieved from their inhibition by regulatory T-cells to help their spread and action against patient's tumor cells. Particularly, TIL are extracted from a patient's tumor, amplified, genetically modified to express an inhibitor of regulatory T-cells, and then re-introduced into the patient as a therapeutic product. Such TIL engineered ex-vivo can be used to treat the original patient (autologous strategy) or another patient who bears the same type of tumor (allogeneic approach). Such method more particularly comprises one or several of the steps of:
a) extracting a tumor-infiltrating lymphocyte from a patient's tumor;
b) expanding said tumor-infiltrating lymphocyte; and
c) introducing into said tumor-infiltrating lymphocyte an exogenous nucleic acid molecule comprising a nucleotide sequence coding for an inhibitor of regulatory T-cell activity.

According to another aspect of the invention, the method can be more particularly applied to T-cells interacting with the pathological cells through a chimeric antigen receptor. Such method more particularly comprises one or several of the steps of:
a) providing a T-cell;
b) introducing into said T-cell an exogenous nucleic acid molecule comprising a nucleotide sequence coding for a first Chimeric Antigen Receptor (CAR) directed against at least one antigen expressed at the surface of a malignant or infected cell; and
c) introducing into said T-cell an exogenous nucleic acid molecule comprising a nucleotide sequence coding for an inhibitor of regulatory T-cells activity.

By "inhibitor of regulatory T-cells" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

According to preferred embodiments, said inhibitor of regulatory T-cell activity is an inhibitor of FoxP3, and more preferably is a cell-penetrating peptide inhibitor of FoxP3, such as that referred as P60 (Casares et al., 2010).

According to preferred embodiments, the engineered T-cell concomitantly expresses a CAR on its surface that binds a surface antigen marker of a pathological cell. This binding has the effect of triggering an immune response by the T-cell directed against the pathological cell, which result into degranulation of various cytokine and degradation enzymes in the interspace between the cells.

According to certain embodiments, the method comprises a further step of introducing into said T-cell an exogenous nucleic acid molecule comprising a nucleotide sequence coding for a second Chimeric Antigen Receptor directed against at least one antigen expressed at the surface of a regulatory T-cell (Treg). After having introduced said nucleic acid, said second Chimeric Antigen Receptor may then be expressed by said T-cell.

Said second CAR is directed against the regulatory T-cells in order to primarily physically maintain said regulatory T-cells in the close environment of the T-cells (and also of the pathological cells) for obtaining in-situ inhibition of the regulatory T-cells. The second CAR can also contribute to activating the T-cells immune response.

According to optional embodiments, the method further comprises the step of making the T-cells non-alloreactive by inactivating at least one gene coding for one component of the T-Cell receptor (TCR). This can be achieved by introducing into the cells a specific rare-cutting endonuclease targeting this gene, such as a TAL-nuclease, a CAS9 RNA guided endonuclease, a Zinc Finger nuclease or a meganuclease.

The present invention thus preferably provides engineered T-cells, in particular, genetically engineered isolated T-cells comprising:
a) an exogenous nucleic acid molecule comprising a nucleotide sequence coding for a first Chimeric Antigen Receptor (CAR) directed against at least one antigen expressed at the surface of a malignant or infected cell; and
b) an exogenous nucleic acid molecule comprising a nucleotide sequence coding for an inhibitor of regulatory T-cell activity, preferably a cell-penetrating peptide inhibitor of FoxP3, such as that referred as P60 (Casares et al., 2010).

According to preferred embodiments, said first Chimeric Antigen Receptor and said inhibitor of regulatory T-cell activity are expressed by said T-cell.

According to other embodiments, the engineered T-cell further comprises c) an exogenous nucleic acid molecule comprising a nucleotide sequence coding for a second Chimeric Antigen Receptor directed against at least one antigen expressed at the surface of a regulatory T-cell (Treg). According to particular embodiments, said second Chimeric Antigen Receptor is expressed by said T-cell.

According to further embodiments, the engineered T-cell further comprises d) an exogenous nucleic acid molecule comprising a nucleotide sequence coding for a rare-cutting endonuclease able to selectively inactivate by DNA cleavage at least one gene coding for one component of the T-Cell receptor (TCR). According to particular embodiments, said rare-cutting endonuclease able to selectively inactivate by DNA cleavage at least one gene coding for one component of the T-Cell receptor (TCR) is expressed by said T-cell. The disruption of TCR provides non-alloreactive T-cells that can be used in allogeneic treatment strategies.

The present invention further provides isolated nucleic acid molecules comprising a nucleotide sequence coding for a Chimeric Antigen Receptor (CAR) directed against at least one antigen expressed at the surface of a malignant or infected cell; and a nucleotide sequence coding for an inhibitor of regulatory T-cell activity, preferably a cell-penetrating peptide inhibitor of FoxP3, such as that referred as P60 (Casares et al., 2010). According to certain embodiments, said nucleic acid molecule is a vector, such as a viral vector or plasmid. More particularly, said nucleic acid molecule is a vector, such as a viral vector or plasmid, and said nucleotide sequences being operatively linked to one or more promoters suitable for expression in a T-cell.

The present invention further provides compositions comprising one or more nucleic acid molecules comprising a nucleotide sequence coding for a first Chimeric Antigen Receptor (CAR) directed against at least one antigen expressed at the surface of a malignant or infected cell; and a nucleotide sequence coding for an inhibitor of regulatory T-cell activity, preferably a cell-penetrating peptide inhibitor of FoxP3, such as that referred as P60 (Casares et al., 2010). According to certain embodiments, the composition comprises a nucleic acid molecule comprising a nucleotide sequence coding for said first Chimeric Antigen Receptor (CAR); and a nucleotide sequence coding for said an inhibitor of regulatory T-cell activity. According to certain other embodiments, the composition comprises a first nucleic acid molecule comprising a nucleotide sequence coding for said first Chimeric Antigen Receptor (CAR) directed against at least one antigen expressed at the surface of a malignant or infected cell; and a second nucleic acid molecule comprising a nucleotide sequence coding for an inhibitor of regulatory T-cell activity, preferably a cell-penetrating peptide inhibitor of FoxP3, such as that referred as P60 (Casares et al., 2010). According to certain embodiments, the composition comprises a further nucleic acid molecule comprising a nucleotide sequence coding for a second Chimeric Antigen Receptor directed against at least one antigen expressed at the surface of a regulatory T-cell (Treg). According to certain embodiments, said nucleic acid molecules are vectors, such as viral vectors or plasmids. More particularly, said nucleic acid molecules are vectors, such as viral vectors or plasmids, and said nucleotide sequences being operatively linked to one or more promoters suitable for expression in a T-cell.

The present invention further provides kits comprising one or more isolated nucleic acid according to the present invention or one or more compositions according to the present invention.

As a result of the present invention, engineered T-cells can be used as therapeutic products, ideally as an "off the shelf" product, for use in the treatment or prevention cancer, bacterial or viral infections, or auto-immune diseases. Thus, the present invention further provides an engineered T-cell or a composition, such as a pharmaceutical composition, comprising same for use as a medicament. According to certain embodiments, the engineered T-cell or composition is for use in the treatment of a cancer, and more particularly for use in the treatment of lymphoma. According to certain other embodiments, the engineered T-cell or composition is for use in the treatment of viral infection. According to certain other embodiments, the engineered T-cell or composition is for use in the treatment of bacterial infection.

It is understood that the details given herein with respect to one aspect of the invention also apply to any of the other aspects of the invention.

DETAILED DESCRIPTION OF THE INVENTION

Figure 1:
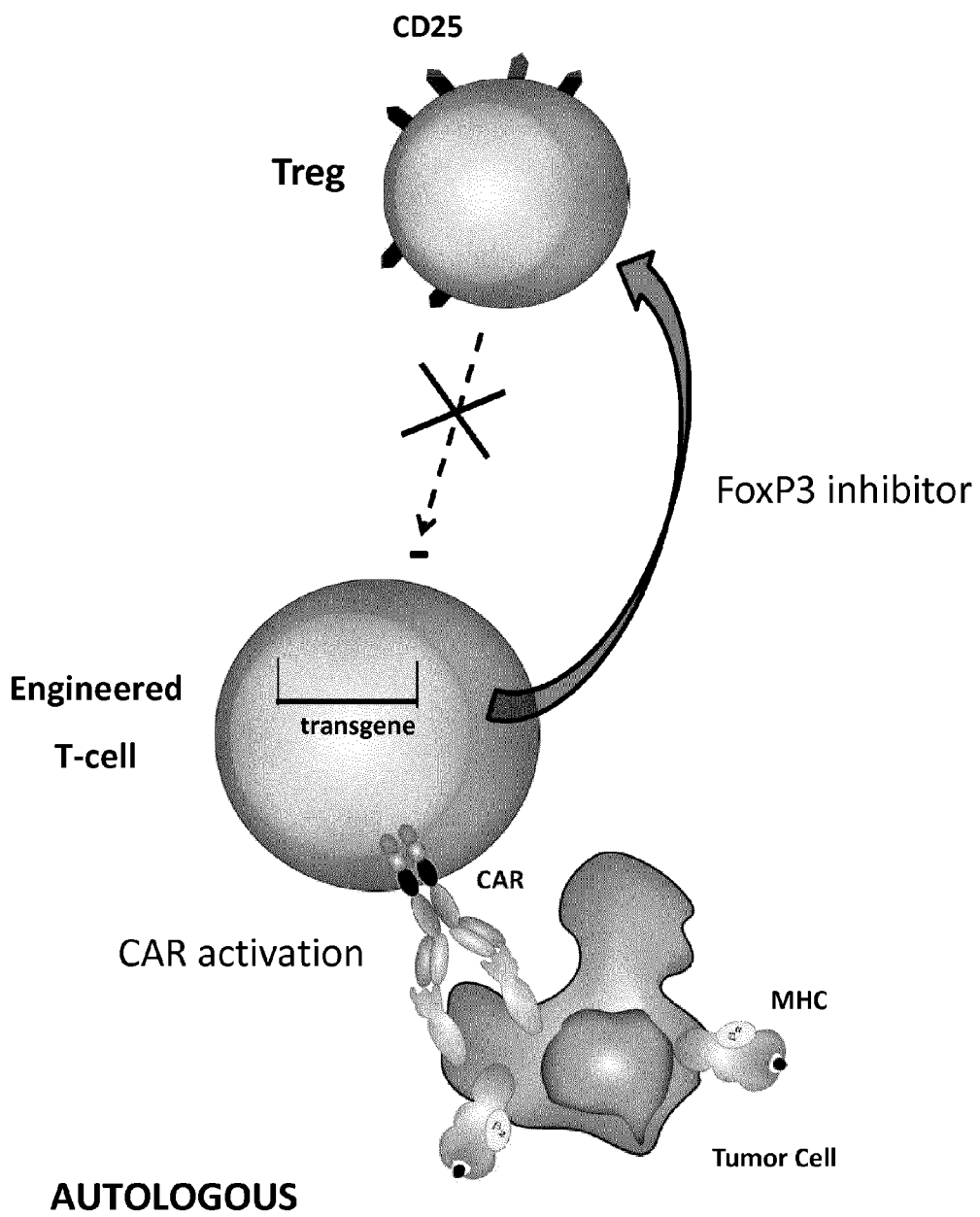
FIG. 1: Schematic representation of the engineered T-cell according the invention expressing both a Chimeric Antigen Receptor (CAR) directed against at least one antigen expressed at the surface of a malignant or infected cell, and a cell-penetrating peptide inhibitor of FoxP3. The peptide inhibitor of FoxP3 expressed and secreted by the engineered T-cell will enter neighbouring regulatory T-cells and prevent them from modulating the anti-tumor or anti-infection response.
Figure 2:
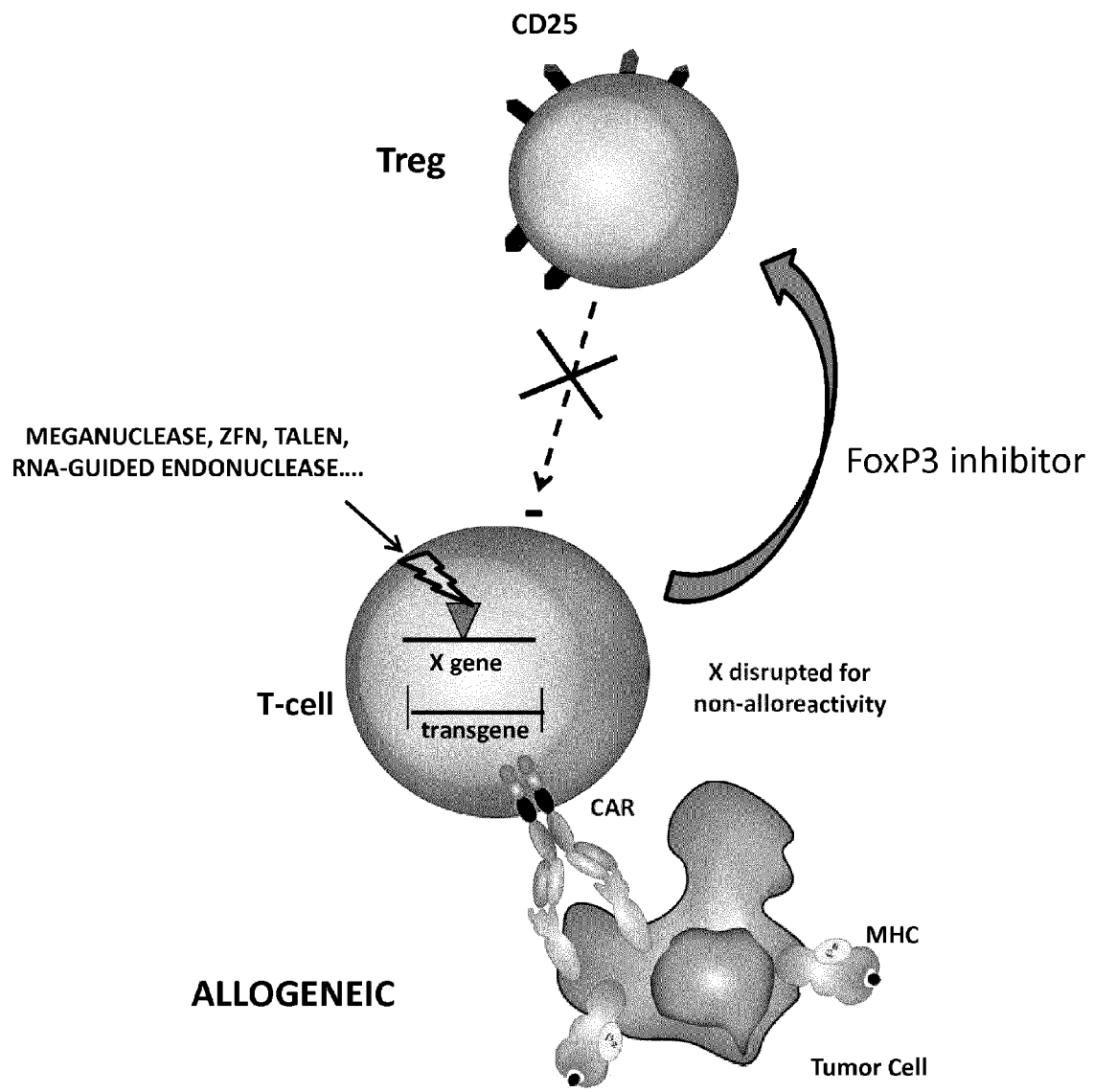
FIG. 2: Schematic representation of an engineered T-cell according the invention expressing a Chimeric Antigen Receptor (CAR) directed against at least one antigen expressed at the surface of a malignant or infected cell, and a cell-penetrating peptide inhibitor of FoxP3 as well as a rare-cutting endonuclease able to selectively inactivate by DNA cleavage at least one gene coding for one component of the T-Cell receptor (TCR). The inactivation of at least one gene coding for a TCR component renders the genetically engineered T-cell non-alloreactive.
Figure 3:
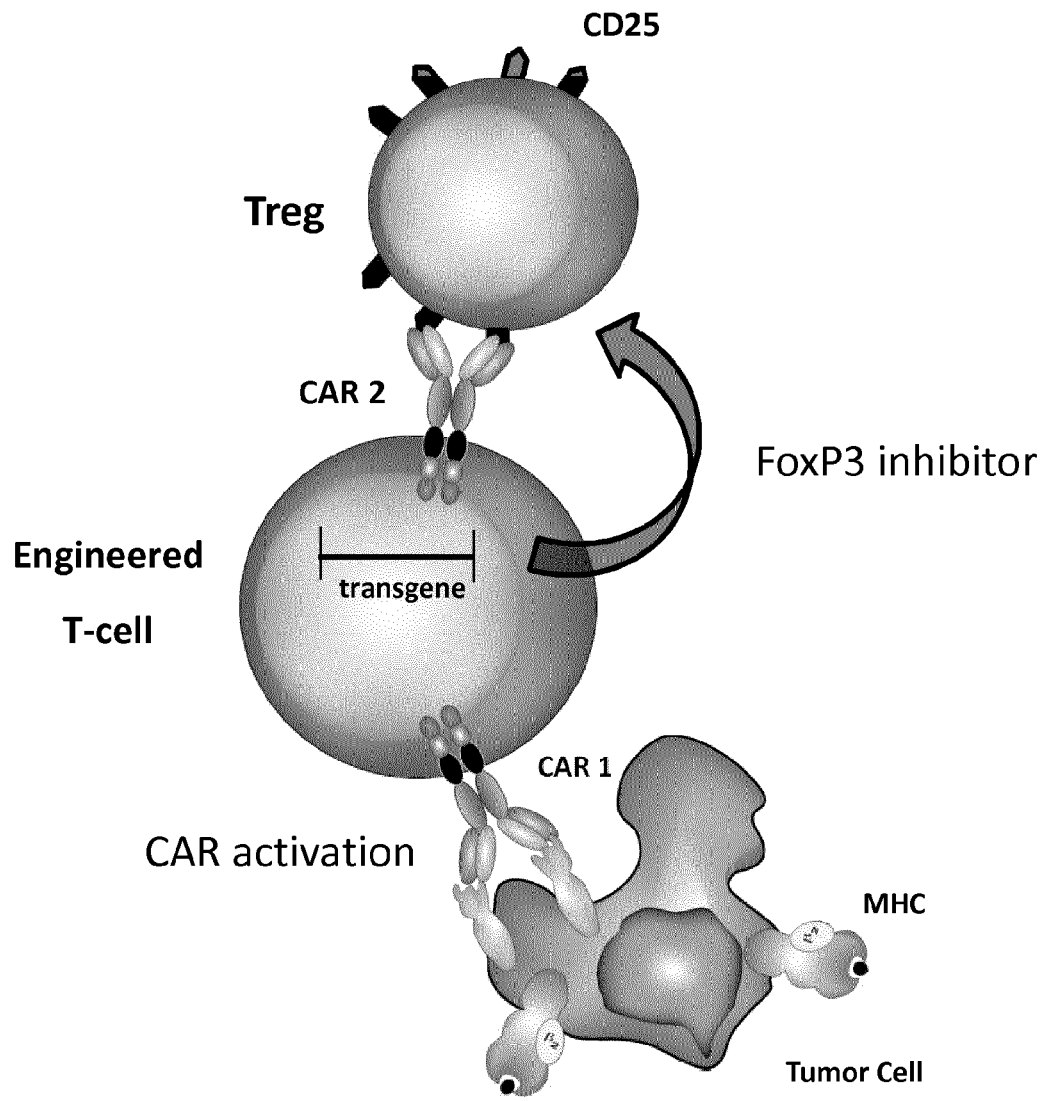
FIG. 3: Schematic representation of an engineered T-cell according the invention expressing a first Chimeric Antigen Receptor directed against at least one antigen expressed at the surface of a malignant or infected cell, a cell-penetrating peptide inhibitor of FoxP3 as well as a second Chimeric Antigen Receptor directed against at least one antigen expressed at the surface of a regulatory T-cell (Treg) which allows the binding of a regulatory T-cell by the engineered T-cell of the invention and facilitates the entry of the peptide inhibitor of FoxP3 into the regulatory T-cell.
Figure 4:
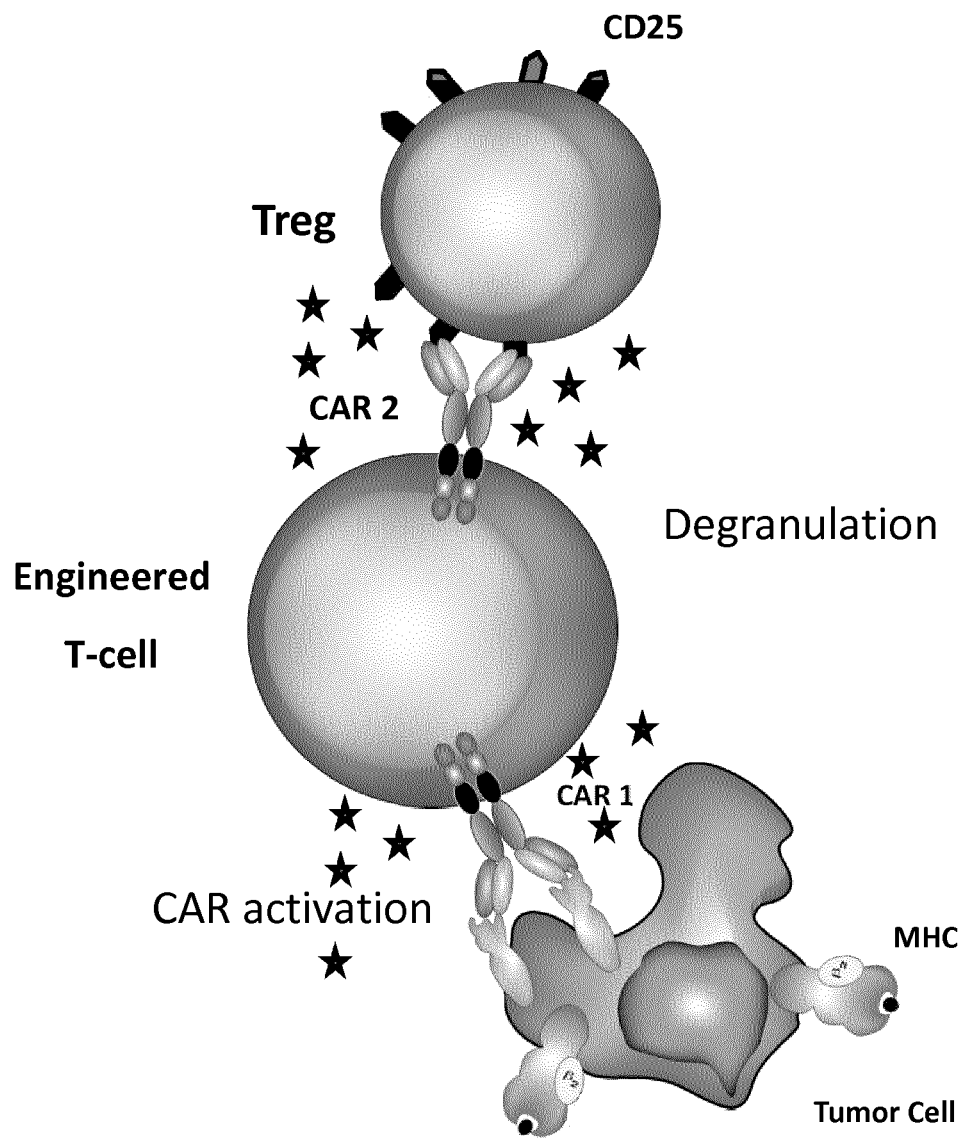
FIG. 4: Schematic representation of an engineered T-cell according the invention expressing a first Chimeric Antigen a first Chimeric Antigen Receptor directed against at least one antigen expressed at the surface of a malignant or infected cell, a cell-penetrating peptide inhibitor of FoxP3 as well as a second Chimeric Antigen Receptor directed against at least one antigen expressed at the surface of a regulatory T-cell (Treg). In this configuration, the engineered T-cell does not necessarily express a transgene that codes for an inhibitor of Treg, but can neutralize Treg by merely specifically binding to them (e.g. CD25 is a specific Treg surface protein).
Figure 5:
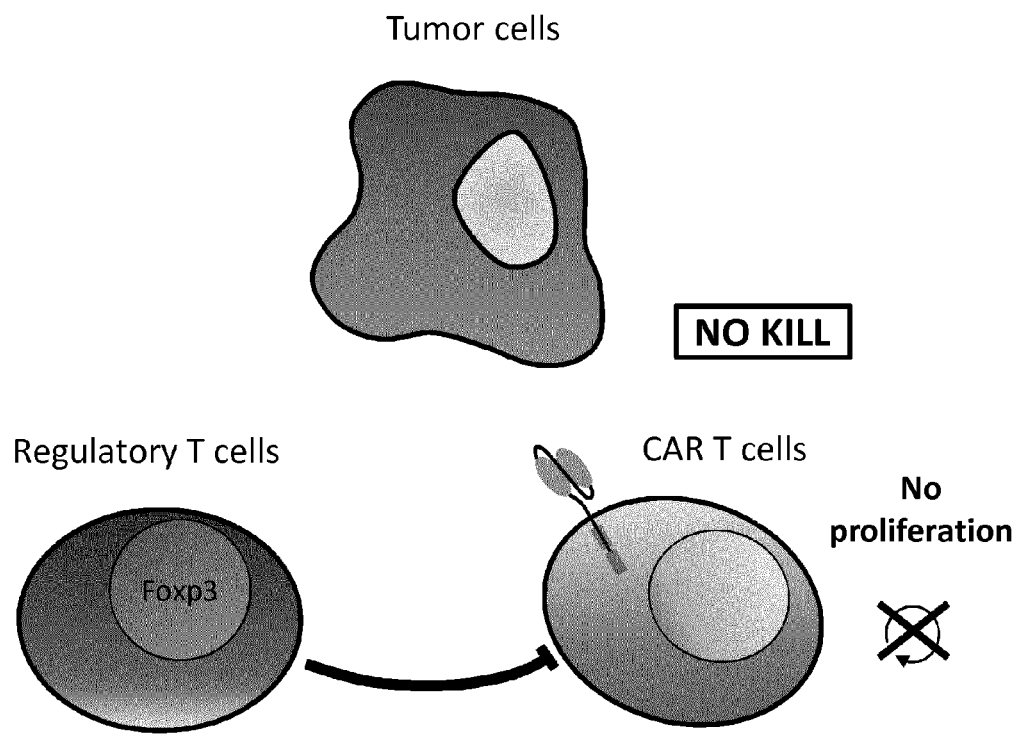
FIG. 5: Schematic representation of an engineered T-cell expressing a first Chimeric Antigen a first Chimeric Antigen Receptor, which cytotoxic activity is inhibited by a Treg.
Figure 6:
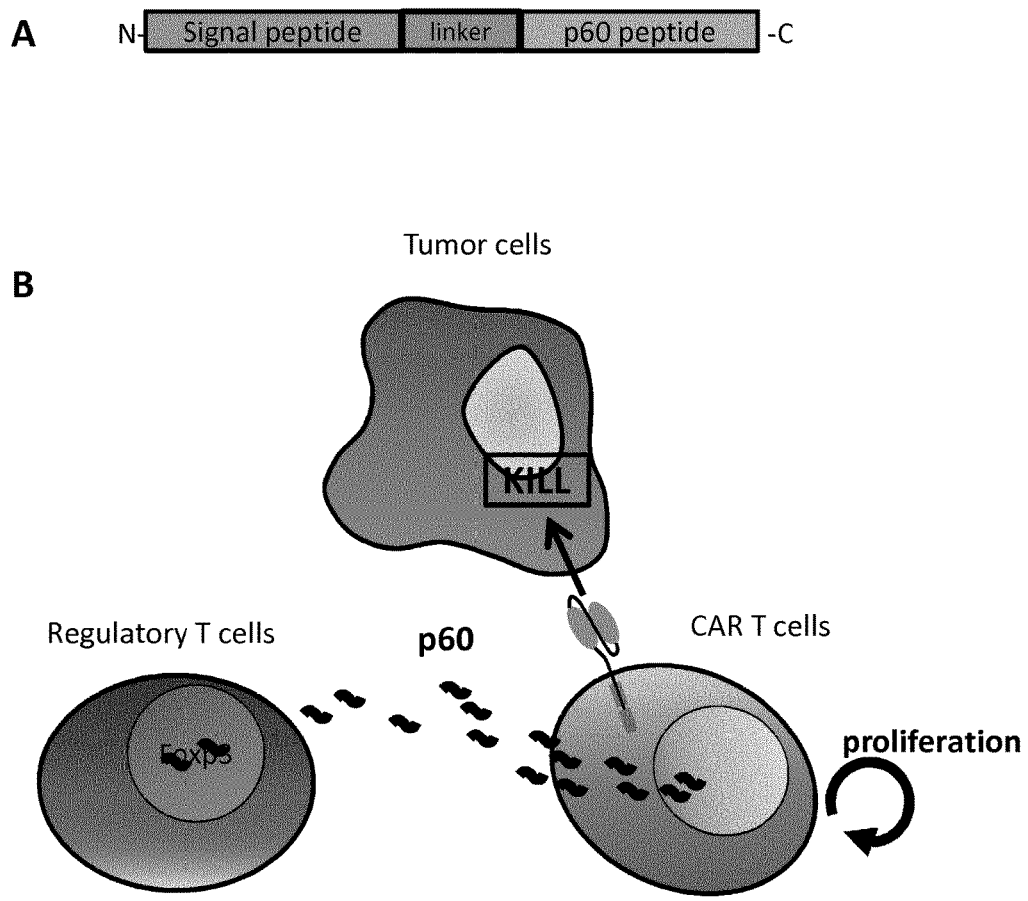
FIG. 6AB: Schematic representation of an engineered T-cell according to the invention expressing a first Chimeric Antigen a first Chimeric Antigen Receptor and overexpressing p60 as a cell-penetrating peptide inhibitor of FoxP3 with the effect that the inhibition by the Treg is lifted and the T cells recovers cytolytic activity against the tumor cells.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Methods for Preparing Engineered T-Cells

In a general aspect, the present invention pertains to methods for preparing engineered T-cells that have the ability to lift their inhibition by Treg, preferably by heterologous expression of an inhibitor of Treg, such as a penetrating peptide inhibitor of FoxP3.

Because regulatory T-cells, also known as suppressor T-cells, play a role in dampening immune responses, in particular to prevent autoimmunity and maintaining tolerance of self-antigens, it is desirable to suppress the activity of this cell type in certain pathogenic situations, such as cancer or chronic infectious diseases, to allow a more potent immune response to occur. In order to allow a local suppression of regulatory T-cells, an inhibitor is secreted by the engineered T-cell, preferably a peptide inhibitor of FoxP3 into the environment of the engineered T-cell(s). This later peptide inhibitor will enter neighbouring regulatory T-cells and prevent them from modulating the immune response by inhibition of FoxP3. The localized delivery of the peptide inhibitor of FoxP3 by the engineered T-cell(s) of the present invention has the great advantage of reducing the possibility of toxic effects such inhibitor would unfold elsewhere in the body.

According to a first aspect, the invention is applied to a subset of T-cells called tumor-infiltrating lymphocytes (TIL), which are found in tumors with the particularity of having developed some affinity to at least a population of tumor cells found in said tumors. Generally, these TILs remain active against the tumor cells and thus are valuable in immunotherapy for treating said tumors (Rosenberg, S A. et al. (1986) A new approach to the adoptive immunotherapy of cancer with tumor-infiltrating lymphocytes. Science. 233 (4770):1318-1321). However, these cells are generally in limited number and are confined to such tumors. The invention allows enhancing their activities and helping their proliferation by proceedings by one or several of the following steps:

Extracting TILs from one or several tumors from one or several patients;

Expanding the TILs to obtain a significant number useful for immunotherapy, preferably up to at least 105 cells, more preferably up to at least 106 cells;

Introducing into the cells a nucleic acid comprising a nucleotide sequence coding for an inhibitor of regulatory T-cell activity;

Further activating and expanding the engineered TILs; and

Infusing the engineered TILs back into the patient or in other patients.

According to another aspect, the T-cells are engineered to express both a Chimeric Antigen Receptor (CAR) directed against at least one antigen expressed at the surface of a malignant or infected cell, herein denoted first CAR, and an inhibitor of regulatory T-cell activity, in particular, a cell-penetrating peptide inhibitor of FoxP3. The CAR will direct the engineered T-cells to the tumor site or site of infection and allows the T-cell(s) to kill the tumor or infected cells.

Accordingly, the present invention provides a method for preparing an engineered T-cell comprising the steps of:

a) providing a T-cell;

b) introducing into said T-cell an exogenous nucleic acid molecule comprising a nucleotide sequence coding for a first Chimeric Antigen Receptor (CAR) directed against at least one antigen expressed at the surface of a malignant or infected cell; and c) introducing into said T-cell an exogenous nucleic acid molecule comprising a nucleotide sequence coding for an inhibitor of regulatory T-cell activity, such as a cell-penetrating peptide inhibitor of FoxP3.

As a result, an engineered T-cell is obtained which expresses a first Chimeric Antigen Receptor (CAR) directed against at least one antigen expressed at the surface of a malignant or infected cell, and an inhibitor of regulatory T-cell activity, such as a cell-penetrating peptide inhibitor of FoxP3.

In addition to the Chimeric Antigen Receptor (CAR) directed against at least one antigen expressed at the surface of a malignant or infected cell, it may be preferable to have a further CAR expressed by the engineered T-cell which is directed against at least one antigen expressed at the surface of a regulatory T-cell (Treg), such as the surface antigen CD25. This will allow the binding of a regulatory T-cell and facilitates the entry of the inhibitor of regulatory T-cell activity. Accordingly, the method may further comprise introducing into said T-cell an exogenous nucleic acid molecule comprising a nucleotide sequence coding for a second Chimeric Antigen Receptor directed against at least one antigen expressed at the surface of a regulatory T-cell (Treg). After having introduced said nucleic acid, said second Chimeric Antigen Receptor may then be expressed by said T-cell.

As a result, an engineered T-cell is obtained which further expresses a second Chimeric Antigen Receptor directed against at least one antigen expressed at the surface of a regulatory T-cell (Treg).

It is also contemplated by the present invention that the engineered T-cell of the present invention further expresses a rare-cutting endonuclease able to selectively inactivate by DNA cleavage at least one gene coding for one component of the T-Cell receptor (TCR). T-cell receptors are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD. The inactivation of at least one gene coding for a TCR component thus renders the genetically engineered T-cell non-alloreactive. By "inactivating" or "inactivation of" a gene it is meant that the gene of interest is not expressed in a functional protein form.

Accordingly, the method of the present invention may further comprise introducing into said T-cell an exogenous nucleic acid molecule comprising a nucleotide sequence coding for a rare-cutting endonuclease able to selectively inactivate by DNA cleavage, preferably double-strand break, at least one gene coding for one component of the T-Cell receptor (TCR). In particular embodiments, the rare-cutting endonuclease is able to selectively inactivate by DNA cleavage the gene coding for TCR alpha or TCR beta.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In a particular embodiment, said rare-cutting endonuclease according to the present invention is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; Mali, Yang et al. 2013). Cas9, also named Csn1 is a large protein that participates in both crRNA biogenesis and in the destruction of invading DNA. Cas9 has been described in different bacterial species such as *S. thermophiles, Listeria innocua* (Gasiunas, Barrangou et al. 2012; Jinek, Chylinski et al. 2012) and *S. Pyogenes* (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold). Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a *S. pyogenes* Cas9 endonuclease (COG3513).

In a particular embodiment, said rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

In a particular embodiment, said rare-cutting endonuclease can be a "Zinc Finger Nucleases" (ZFNs), which are generally a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (Genome editing with engineered zinc finger nucleases (2010) *Nature reviews Genetics* 11:636-646). Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp. The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

In a particular embodiment, said rare-cutting endonuclease is a "TALE-nuclease" or a "MBBBD-nuclease" resulting from the fusion of a DNA binding domain typically derived from Transcription Activator Like Effector proteins (TALE) or from a Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France). In general, the DNA binding domain is derived from a Transcription Activator like Effector (TALE), wherein sequence specificity is driven by a series of 33-35 amino acids repeats originating from *Xanthomonas* or *Ralstonia* bacterial proteins AvrBs3, PthXo1, AvrHah1, PthA, Tal1c as non-limiting examples. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. Other modular base-per-base specific nucleic acid binding domains (MBBBD) are described in WO 2014/018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica*. These nucleic acid binding polypeptides comprise modules of about 31 to 33 amino acids that are base specific. These modules display less than 40 sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins. As a result, an engineered T-cell is obtained which further expresses a rare-cutting endonuclease able to selectively inactivate by DNA cleavage at least one gene coding for one component of the T-Cell receptor (TCR).

It is also contemplated by the present invention that the engineered T-cell of the present invention further expresses a rare-cutting endonuclease able to selectively inactivate by DNA cleavage, preferably double-strand break, the gene coding for the surface antigen CD25. By inactivating the gene coding for CD25 the engineered T-cells are unlikely to self-associate or to self-interact and prevented from targeting T-cells other than Treg.

The T-cell to be modified according to the present invention may be any suitable T-cell. For example, the T-cell can be an inflammatory T-lymphocyte, cytotoxic T-lymphocyte, or helper T-lymphocyte. Particularly, the T-cell is a cytotoxic T-lymphocyte. In certain embodiments, said T-cell is selected from CD4+ T-lymphocytes and CD8+ T-lymphocytes. In particular embodiments, the T-cell to be modified according to the present invention is a human T-cell. Prior to expansion and genetic modification of the cells of the invention, a source of cells can be obtained from a subject, such as a patient, through a variety of non-limiting methods. T-cell can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics.

In accordance with the present invention, the nucleic acid molecules detailed herein may be introduced in the T-cell by any suitable methods known in the art. Suitable, non-limiting methods for introducing a nucleic acid molecule into a T-cell according include stable transformation methods, wherein the nucleic acid molecule is integrated into the genome of the cell, transient transformation methods wherein the nucleic acid molecule is not integrated into the genome of the cell and virus mediated methods. Said nucleic acid molecule may be introduced into a cell by, for example, a recombinant viral vector (e.g., retroviruses, adenoviruses), liposome and the like. Transient transformation methods include, for example, microinjection, electroporation or particle bombardment. In certain embodiments, the nucleic acid molecule is a vector, such as a viral vector or plasmid. Suitably, said vector is an expression vector enabling the expression of the respective polypeptide(s) or protein(s) detailed herein by the T-cell.

A nucleic acid molecule introduced into the T-cell may be DNA or RNA. In certain embodiments, a nucleic acid molecule introduced into the T-cell is DNA. In certain embodiments, a nucleic acid molecule introduced into the T-cell is RNA, and in particular an mRNA encoding a polypeptide or protein detailed herein, which mRNA is introduced directly into the T-cell, for example by electroporation. A suitable electroporation technique is described, for example, in International Publication WO2013/176915 (in particular the section titled "Electroporation" bridging pages 29 to 30). A particular nucleic acid molecule which may be an mRNA is the nucleic acid molecule comprising a nucleotide sequence coding for a rare-cutting endonuclease able to selectively inactivate by DNA cleavage at least one gene coding for one component of the T-Cell Receptor (TCR).

Peptide Inhibitor of FoxP3

The peptide inhibitor of FoxP3 in accordance with the present invention may be any peptide or polypeptide capable of inhibiting the activity of the forkhead/winged helix transcription factor 3 (FoxP3, preferably human FoxP3), a transcription factor specific for regulatory T-cells and required for their development and function. With "inhibiting" is meant that the activity of FoxP3 in regulatory T-cells is reduced by at least 10%, such as at least 20%, at least 30%, at least 40%, at least 50%, at least 60%, at least 70%, at least 80, at least 90%, at least 95%, at least 99% or 100%. In this respect, "activity of FoxP3" means transcriptional activity.

Moreover, in addition to having a FoxP3 inhibitory activity, the peptide inhibitor of FoxP3 in accordance of the present invention, is capable of penetrating a cell membrane. This functionality may be inherent to the peptide inhibitor of FoxP3 or may be the result of fusing a known cell-penetrating peptide (CPP) and a peptide or polypeptide having FoxP3 inhibitory activity. Said CPP sequence may be N-terminally or C-terminally linked to the amino acid sequence providing for the FoxP3 inhibitory activity. Suitable examples for CPPs include, but are not limited to: Tat, a nuclear transcriptional activator protein which is a 101 amino acid protein required for viral replication by human immunodeficiency virus type 1 (HIV-1), penetratin, which corresponds to the third helix of the homeoprotein Antennapedia in *Drosophila*, Kaposi fibroblast growth factor (FGF) signal peptide sequence, integrin β3 signal peptide sequence; Guanine rich-molecular transporters, MPG, pep-1, sweet arrow peptide, dermaseptins, transportan, pVEC, Human calcitonin, mouse prion protein (mPrPr), polyarginine peptide Args sequence, VP22 protein from Herpes Simplex Virus, antimicrobial peptides Buforin I and SynB (US2013/0065314).

A non-limiting example of peptide inhibitor of FoxP3 in accordance with the present invention is the polypeptide P60 described by Casares et al. (2010). In addition to its FoxP3 inhibitory activity, it has been shown that P60 is also able to penetrate a cell membrane. This polypeptide has the amino acid sequence: RDFQSFRKMWPFFAM [SEQ ID NO: 1]. An illustrative nucleotide sequence coding for this polypeptide is represented by CGCGACTTTCAAAGTTTCCG-TAAGATGTGGCCGTTTTTTGCAATG [SEQ ID NO: 2]. However, it is understood that due to the degeneration of the genetic code any other suitable nucleotide sequence coding for the amino acid sequence set forth in SEQ ID NO: 1 is also encompassed by the present disclosure.

Accordingly, in certain embodiments of the invention, the cell-penetrating peptide inhibitor of FoxP3 is a polypeptide comprising the amino acid sequence set forth in SEQ ID NO: 1 or a variant thereof comprising an amino acid sequence that has at least 60%, such as at least 80%, at least 85%, at least 90% or at least 95%, sequence identity with the amino acid sequence set forth in SEQ ID NO: 1 over the entire length of SEQ ID NO: 1. Hence, in accordance with these embodiments, an exogenous nucleic acid molecule comprising a nucleotide sequence coding for a polypeptide comprising the amino acid sequence set forth in SEQ ID NO: 1 or a variant thereof comprising an amino acid sequence that has at least 60%, such as at least 80%, at least 85%, at least 90% or at least 95%, sequence identity with the amino acid sequence set forth in SEQ ID NO: 1 over the entire length of SEQ ID NO: 1 is introduced into the T-cell. The variant may comprise an amino acid sequence which has one or more, such as two, three, four, five or six amino acid substitutions compared to SEQ ID NO: 1. Preferably, such amino acid substitution is a conservative substitution which means that one amino acid is replaced by another one that is similar in size and chemical properties. Such conservative amino acid substitution may thus have minor effects on the peptide structure and can thus be tolerated without compromising function. Preferably, such variant is capable of inhibiting the activity of FoxP3 and is capable of penetrating a cell membrane.

In accordance with certain embodiments, the exogenous nucleic acid molecule may thus comprise the nucleotide sequence set forth in SEQ ID NO: 2 or any other nucleotide sequence which due to the degeneration of the genetic code also codes for the amino acid sequence set forth in SEQ ID NO: 1.

As a result, an engineered T-cell may be obtained which expresses a polypeptide comprising the amino acid sequence set forth in SEQ ID NO: 1 or a variant thereof comprising an amino acid sequence that has at least 60%, such as at least 80%, at least 85%, at least 90% or at least 95%, sequence identity with the amino acid sequence set forth in SEQ ID NO: 1 over the entire length of SEQ ID NO: 1.

According to certain embodiments of the invention, the cell-penetrating peptide inhibitor of FoxP3 is a polypeptide comprising the amino acid sequence MRDFQSFRKM-WPFFAM [SEQ ID NO: 3] or a variant thereof comprising an amino acid sequence that has at least 60%, such as at least 80% sequence identity with the amino acid sequence set forth in SEQ ID NO: 3 over the entire length of SEQ ID NO: 3. Hence, in accordance with these embodiments, an exogenous nucleic acid molecule comprising a nucleotide sequence coding for a polypeptide comprising the amino acid sequence set forth in SEQ ID NO: 3 or a variant thereof comprising an amino acid sequence that has at least 60%, such as at least 62.5%, at least 75% or at least 87.5% sequence identity with the amino acid sequence set forth in SEQ ID NO: 3 over the entire length of SEQ ID NO: 3 is introduced into the T-cell. The polypeptide comprising an amino acid sequence that has at least 60% sequence identify with the amino acid sequence set forth in SEQ ID NO: 3 over the entire length of SEQ ID NO: 3 may comprise an amino acid sequence which has one or more, such as two, three, four, five or six amino acid substitutions compared to SEQ ID NO: 3. Preferably, such amino acid substitution is a conservative substitution which means that one amino acid is replaced by another one that is similar in size and chemical properties. Such conservative amino acid substitution may thus have minor effects on the peptide structure and can thus be tolerated without compromising function. Preferably, such variant is capable of inhibiting the activity of FoxP3 and is capable of penetrating a cell membrane.

In accordance with certain embodiments, the exogenous nucleic acid molecule may thus comprise the nucleotide sequence ATGCGCGACTTTCAAAGTTTCCGTAAGAT-GTGG CCGTTTTTTGCAATG [SEQ ID NO: 4] or any other nucleotide sequence which due to the degeneration of the genetic code also codes for the amino acid sequence set forth in SEQ ID NO: 3.

As a result, an engineered T-cell may be obtained which expresses a polypeptide comprising the amino acid sequence set forth in SEQ ID NO: 3 or a variant thereof comprising an amino acid sequence that has at least 60%, such as at least 62.5%, at least 75% or at least 87.5% sequence identity with the amino acid sequence set forth in SEQ ID NO: 3 over the entire length of SEQ ID NO: 3.

Chimeric Antigen Receptors (CARs)

Adoptive immunotherapy, which involves the transfer of autologous antigen-specific T-cells generated ex vivo, is a promising strategy to treat cancer or viral infections. The T-cells used for adoptive immunotherapy can be generated either by expansion of antigen-specific T cells or redirection of T cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T cells has been shown to be successful in treating melanoma.

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

CD19 is an attractive target for immunotherapy because the vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. Most infuse T cells genetically modified to express a chimeric antigen receptor (CAR) with specificity derived from the scFv region of a CD19-specific mouse monoclonal antibody FMC63 (WO2013/126712).

Therefore, in accordance with certain embodiments, the first Chimeric Antigen Receptor is directed against the B-lymphocyte antigen CD19.

In accordance with certain embodiments, the first Chimeric Antigen Receptor is a single chain Chimeric Antigen Receptor. As an example of single-chain Chimeric Antigen Receptor to be expressed in the engineered T-cells according to the present invention is a single polypeptide that comprises at least one extracellular ligand binding domain, a transmembrane domain and at least one signal transducing domain, wherein said extracellular ligand binding domain comprises a scFV derived from the specific anti-CD19 monoclonal antibody 4G7. Once transduced into the T-cell, for instance by using retroviral or lentiviral transduction, this CAR contributes to the recognition of CD19 antigen present at the surface of malignant B-cells involved in lymphoma or leukemia.

In accordance with particular embodiments, the first Chimeric Antigen Receptor is a polypeptide comprising the amino acid sequence forth in SEQ ID NO: 5 or a variant thereof comprising an amino acid sequence that has at least 70%, such as at least 80%, at least 90%, at least 95%, or at least 99%, sequence identity with the amino acid sequence set forth in SEQ ID NO: 5 over the entire length of SEQ ID NO: 5. Preferably, the variant is capable of binding CD19.

In accordance with other certain embodiments, the first Chimeric Antigen Receptor may be directed against another antigen expressed at the surface of a malignant or infected cell, such as a cluster of differentiation molecule, such as CD16, CD64, CD78, CD96, CLL1, CD116, CD117, CD71, CD45, CD71, CD123 and CD138, a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), multiple myeloma or lymphoblastic leukaemia antigen, such as one selected from TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708), and FCRL5 (UNIPROT Q68SN8), a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface antigens.

In other certain embodiments, the first Chimeric Antigen Receptor is a multi-chain Chimeric Antigen Receptor. Chimeric Antigen Receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions as described in WO 2013/176916.

Accordingly, a CAR expressed by the genetically engineered T-cell according to the invention can be a multi-chain chimeric antigen receptor particularly adapted to the production and expansion of engineered T-cells of the present invention. Such multi-chain CARs comprise at least two of the following components:
a) one polypeptide comprising the transmembrembrane domain of FcεRI alpha chain and an extracellular ligand-binding domain,
b) one polypeptide comprising a part of N- and C-terminal cytoplasmic tail and the transmembrane domain of FcεRI beta chain and/or
c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently detailed by the applicant in PCT/US2013/058005.

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR.

The signal transducing domain or intracellular signaling domain of the multi-chain CAR(s) of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. According to particular embodiments, the signaling transducing domain of the multi-chain CAR can comprise the CD3zeta signaling domain, or the intracytoplasmic domain of the FcεRI beta or gamma chains.

According to particular embodiments, the signal transduction domain of multi-chain CARs of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies.

In accordance with particular embodiments, the first Chimeric Antigen Receptor is a polypeptide comprising the amino acid sequence set forth in SEQ ID NO: 6 (encoded by, e.g., SEQ ID NO: 7) or a variant thereof comprising an amino acid sequence that has at least 70%, such as at least 80%, at least 90%, at least 95%, or at least 99%, sequence identity with the amino acid sequence set forth in SEQ ID NO: 6 over the entire length of SEQ ID NO: 6. Preferably, the variant is capable of binding CD19.

A particularly preferred first Chimeric Antigen Receptor is a polypeptide comprising the amino acid sequence set forth in SEQ ID NO: 8 or a variant thereof comprising an amino acid sequence that has at least 80%, such as at least 90%, at least 95%, or at least 99%, sequence identity with the amino acid sequence set forth in SEQ ID NO: 8 over the entire length of SEQ ID NO: 8. Preferably, said variant is capable of binding CD19.

Also encompassed by the present invention are bispecific or multi-specific CARs as described, for instance, in International Publication WO 2014/4011988. Such bi-specific or multi-specific CARs are particularly contemplated with respect to the second CAR which is directed against at least one antigen expressed at the surface of a regulatory T-cell.

A suitable target antigen for the second CAR is the surface antigen CD25, which is known to be expressed on the surface of regulatory T-cells. This will allow the binding of a regulatory T-cell by the engineered T-cell of the invention. Other exemplary surface antigens may be CD4, CD152, IL3R, CCR4, CCR6, CD161 and CXR3.

According to certain embodiments, the second Chimeric Antigen Receptor is mono-specific and, preferably, is directed against surface antigen CD25.

According to other certain embodiments, the second Chimeric Antigen Receptor is bi-specific. According to particular embodiments, such bi-specific second Chimeric Antigen Receptor is directed against surface antigen CD25 and one other surface antigen selected from the group consisting of CD4, CD152, IL3R, CCR4, CCR6, CD161 and CXR3.

As with the first Chimeric Antigen Receptor, the second Chimeric Antigen Receptor may be a single chain Chimeric Antigen Receptor or a multi-chain CAR. The details provided above with respect to the single chain and multi-chain CARs apply mutatis mutandis.

Activation and Expansion of T-Cells

Whether prior to or after genetic modification of the T-cell(s), the T-cell(s) can be activated and expanded generally using methods as described, for example, in U.S. Pat. Nos. 6,352,694; 6,534,055; 6,905,680; 6,692,964; 5,858, 358; 6,887,466; 6,905,681; 7,144,575; 7,067,318; 7,172, 869; 7,232,566; 7,175,843; 5,883,223; 6,905,874; 6,797, 514; 6,867,041; and U.S. Patent Application Publication No. 20060121005. The T-cell(s) may be expanded in vitro or in vivo.

Generally, the T-cell(s) of the invention is expanded by contact with a surface having attached thereto an agent that stimulates a CD3 TCR complex associated signal and a ligand that stimulates a co-stimulatory molecule on the surface of the T cells. In particular, T-cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a T-cell or population of T-cells can be contacted with an anti-CD3 antibody and an anti-CD28 antibody, under conditions appropriate for stimulating proliferation of the T-cells.

In further embodiments of the present invention, the T-cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti- CD28 are attached (3×28 beads) to contact the T cells. According to one embodiment, the cells (for example, 4 to 10 T-cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, −10, −2, 1L-15, TGFp, and TNF—or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

In another particular embodiment, the T-cells may be expanded by co-culturing with tissue or cells. Said T-cells may also be expanded in vivo, for example in the subject's blood after administrating said cell into the subject.

Engineered T-Cells

As a result of the present invention, engineered T-cells can be obtained having improved characteristics. In particular, the present invention provides an engineered, preferably isolated, T-cell which is characterized by the expression of both a Chimeric Antigen Receptor (CAR) directed against at least one antigen expressed at the surface of a malignant or infected cell, herein denoted first CAR, and an inhibitor of regulatory T-cell activity, preferably a cell-penetrating peptide inhibitor of FoxP3.

More particularly, the present invention provides an engineered, preferably isolated, T-cell which comprises:

a) an exogenous nucleic acid molecule comprising a nucleotide sequence coding for a first Chimeric Antigen Receptor (CAR) directed against at least one antigen expressed at the surface of a malignant or infected cell; and b) an exogenous nucleic acid molecule comprising a nucleotide sequence coding for an inhibitor of regulatory T-cell activity, preferably a cell-penetrating peptide inhibitor of FoxP3.

According to certain embodiments, the engineered T-cell further comprises c) an exogenous nucleic acid molecule comprising a nucleotide sequence coding for a second Chimeric Antigen Receptor directed against at least one antigen expressed at the surface of a regulatory T-cell (Treg). According to particular embodiments, said second Chimeric Antigen Receptor is expressed by said T-cell.

According to certain embodiments, the engineered T-cell further comprises d) an exogenous nucleic acid molecule comprising a nucleotide sequence coding for a rare-cutting endonuclease able to selectively inactivate by DNA cleavage at least one gene coding for one component of the T-Cell receptor (TCR). According to particular embodiments, said rare-cutting endonuclease able to selectively inactivate by DNA cleavage at least one gene coding for one component of the T-Cell receptor (TCR) is expressed by said T-cell.

According to certain embodiments, the engineered T-cell further comprises e) an exogenous nucleic acid molecule comprising a nucleotide sequence coding for a rare-cutting endonuclease able to selectively inactivate by DNA cleavage the gene coding for the surface antigen CD25. According to particular embodiments, said rare-cutting endonuclease able to selectively inactivate by DNA cleavage the gene coding for the surface antigen CD25 is expressed by said T-cell.

It is understood that the details given herein in particularly with respect to the first Chimeric Antigen Receptor, the inhibitor of regulatory T-cell activity, especially the cell-penetrating peptide inhibitor of FoxP3, the second Chimeric Antigen Receptor, the rare-cutting endonuclease able to selectively inactivate by DNA cleavage at least one gene coding for one component of the T-Cell receptor (TCR) and the rare-cutting endonuclease able to selectively inactivate by DNA cleavage the gene coding for the surface antigen CD25 also apply to this aspect of the invention.

Further, in the scope of the present invention is also encompassed a cell line obtained from a genetically engineered T-cell according to the invention.

Nucleic Acids, Compositions and Kits

In further aspects, the present invention provides nucleic acid molecules suitable for expressing the various CARs, the inhibitor of regulatory T-cell activity, especially the peptide inhibitors FoxP3, and endonucleases in a T-cell as well as compositions and kits comprising such nucleic acid molecules.

Accordingly, the present invention provides an isolated nucleic acid molecule comprising a nucleotide sequence coding for a Chimeric Antigen Receptor (CAR) directed against at least one antigen expressed at the surface of a malignant or infected cell; and a nucleotide sequence coding for an inhibitor of regulatory T-cell activity, preferably a cell-penetrating peptide inhibitor of FoxP3.

The nucleic acid molecule may be DNA or RNA. In certain embodiments, the nucleic acid molecule is DNA. In certain other embodiments, the nucleic acid molecule is RNA molecule, and in particular an mRNA encoding said Chimeric Antigen Receptor and said cell-penetrating peptide inhibitor of FoxP3. In accordance with particular embodiments, the nucleotide sequence coding for said Chimeric Antigen Receptor (CAR) and the nucleotide sequence coding for an inhibitor of regulatory T-cell activity, preferably a cell-penetrating peptide inhibitor of FoxP3, are operatively linked to each other by a nucleotide sequence coding for ribosomal skip sequence, such as a nucleotide sequence coding for a 2A peptide. Such ribosomal skip mechanisms are well known in the art and are known to be used by several vectors for the expression of several proteins encoded by a single mRNA.

In accordance with certain embodiments, the nucleic acid is a vector, such as a viral vector or plasmid. In order to allow expression by the T-cell the nucleotide sequence coding for said Chimeric Antigen Receptor (CAR) and the nucleotide sequence coding for an inhibitor of regulatory T-cells activity, preferably a cell-penetrating peptide inhibitor of FoxP3, are operatively linked to one or more promoters suitable for expression in a T-cell. In some cases it may be desirable to have the inhibitor of regulatory T-cells activity, such as the cell-penetrating peptide inhibitor of FoxP3, only expressed if the Chimeric Antigen Receptor recognizes and binds the antigen to which it is specific. In such cases, the expression of the cell-penetrating peptide inhibitor of FoxP3 is preferably under the control of an inducible promoter, such as a NFAT minimal promoter.

Also encompassed within the scope of the invention are compositions which comprise one or more of the nucleic acid molecules detailed herein. Particularly, the present invention provides compositions comprising one or more nucleic acid molecules comprising a nucleotide sequence coding for a first Chimeric Antigen Receptor (CAR) directed against at least one antigen expressed at the surface of a malignant or infected cell; and a nucleotide sequence coding for a cell-penetrating peptide inhibitor of FoxP3. In accordance with certain embodiments, a composition is provided which comprises a nucleic acid molecule comprising a nucleotide sequence coding for said first Chimeric Antigen Receptor (CAR); and a nucleotide sequence coding for said an inhibitor of regulatory T-cell activity, preferably said cell-penetrating peptide inhibitor of FoxP3. In accordance with other certain embodiments, a composition is provided which comprises a first nucleic acid molecule comprising a nucleotide sequence coding for said first Chimeric Antigen Receptor (CAR) directed against at least one antigen expressed at the surface of a malignant or infected cell; and a second nucleic acid molecule comprising a nucleotide sequence coding for an inhibitor of regulatory T-cell activity, preferably said cell-penetrating peptide inhibitor of FoxP3. In accordance with particular embodiments, the composition may comprise a further nucleic acid molecule comprising a nucleotide sequence coding for a second Chimeric Antigen Receptor directed against at least one antigen expressed at the surface of a regulatory T-cell (Treg). In accordance with other particular embodiments, composition may comprise a further nucleic acid molecule comprising a nucleotide sequence coding for a rare-cutting endonuclease able to selectively inactivate by DNA cleavage at least one gene coding for one component of the T-Cell receptor (TCR) and/or a nucleic acid molecule comprising a nucleotide sequence coding for a rare-cutting endonuclease able to selectively inactivate by DNA cleavage the gene coding for the surface antigen CD25.

The nucleic acid molecule(s) comprised by the compositions may be DNA or RNA. In certain embodiments, a nucleic acid molecule is DNA. In certain other embodiments, a nucleic acid molecule is RNA molecule. In accordance certain embodiments, the nucleic acid molecule or nucleic acid molecules are vectors, such as viral vectors or plasmids. In order to allow expression by the T-cell the nucleotide sequence coding for said Chimeric Antigen Receptor (CAR) and/or the nucleotide sequence coding for an inhibitor of regulatory T-cell activity, preferably a cell-penetrating peptide inhibitor of FoxP3, are operatively linked to one or more promoters suitable for expression in a T-cell.

Also encompassed within the scope of the invention are kits comprising one or more of the nucleic acid molecules or one or more compositions detailed herein.

It is understood that the details given herein in particularly with respect to the first Chimeric Antigen Receptor, the inhibitor of regulatory T-cell activity, especially the cell-penetrating peptide inhibitor of FoxP3, the second Chimeric Antigen Receptor, the rare-cutting endonuclease able to selectively inactivate by DNA cleavage at least one gene coding for one component of the T-Cell receptor (TCR) and the rare-cutting endonuclease able to selectively inactivate by DNA cleavage the gene coding for the surface antigen CD25 also apply to these aspects of the invention.

Therapeutic Applications

The T-cells obtainable in accordance with the present invention are intended to be used as a medicament, and in particular for treating, among others, cancer, infections (such viral infections) or immune diseases in a patient in need thereof. Accordingly, the present invention provides engineered T-cells for use as a medicament. Particularly, the present invention provides engineered T-cells for use in the treatment of a cancer, such as lymphoma, or viral infection. Also provided are compositions, particularly pharmaceutical compositions, which comprise at least one genetically engineered T-cell of the present invention. In certain embodiments, a composition may comprise a population of engineered T-cell of the present invention.

The treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T-cells may be pooled and administrated to one or several patients, being made available as an "off the shelf" therapeutic product.

The treatments are primarily to treat patients diagnosed with cancer. Cancers are preferably leukemias and lymphomas, which have liquid tumors, but may also concern solid tumors. Types of cancers to be treated with the genetically engineered T-cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The treatment can take place in combination with one or more therapies selected from the group of antibodies therapy, chemotherapy, cytokines therapy, dendritic cell therapy, gene therapy, hormone therapy, laser light therapy and radiation therapy.

According to certain embodiments, T-cells of the invention can undergo robust in vivo T-cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In other embodiments, said effective amount of cells or composition comprising those cells are administered parenterally. Said administration can be an intravenous administration. Said administration can be directly done by injection within a tumor.

In certain embodiments, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 11; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded genetically engineered T-cells of the present invention. In an additional embodiment, expanded cells are administered before or following surgery.

Also encompassed within this aspect of the invention are methods for treating a patient in need thereof, comprising a) providing at least one engineered T-cell of the present invention, preferably a population of said T-cell; and b) administering said T-cell or population to said patient.

Also encompassed within this aspect of the invention are methods for preparing a medicament using at least one engineered T-cell of the present invention, and preferably a population of said T-cell. Accordingly, the present invention provides the use of at least one engineered T-cell of the present invention, and preferably a population of said T-cell, in the manufacture of a medicament. Preferably, such medicament is for use in the treatment of a cancer, such as lymphoma, or viral infection.

OTHER DEFINITIONS

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures. Preferably, the cell or cells are human cells.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended an active mutant of a protein, polypeptide or a protein domain; such mutant may have the same activity compared to its parent protein, polypeptide or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base or amino acid, then the molecules are identical at that position. A degree of similarity or identity between nucleic acid or amino acid sequences is a function of the number of identical or matching nucleotides or amino acids at positions shared by the nucleic acid or amino acid sequences, respectively. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory μg and (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non-limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

EXAMPLES

Example 1: Treg Inhibition Test

Human primary T cells were activated with anti-CD3/CD28 beads. At day 3, they were transfected with a messenger RNA coding for foxp3 inhibitory peptide p60 (SEQ ID NO: 1) fused to a mutated Chicken lysozyme signal peptide (3R CLSP—SEQ ID NO: 12) (alternative SEQ ID NO. 13 to 17 displayed in Table 1 may also be used). At day four, the transfected T cells were mixed with human regulatory T cells (Treg) and their proliferation was followed according to the assay described by Collison, L. W et al. (In vitro Treg suppression assays, Methods Mol. Biol., 2011, 707:21-37). This assay shows that the T-cells transfected with the p60 messenger RNAs, proliferate faster than those transfected with the mock RNA (scrambled p60—SEQ ID NO: 9), upon contact with the regulatory T cells. It resulted that p60 peptide expression allowed T cells to resist Treg inhibition.

Example 2: Cytotoxic Activity Test

Human primary T cells is activated with anti-CD3/CD28 beads. At day 3, the activated T cells are transduced with a lentiviral vector encoding the chimeric antigen receptor anti-CD19 set forth as SEQ ID NO: 5 along with the Foxp3 inhibitory peptide p60 (SEQ ID NO: 1) fused to a mutated Chicken lysozyme signal peptide (3R CLSP—SEQ ID NO: 12) (alternative SEQ ID NO. 13 to 17 displayed in Table 1 may also be used). At day 5, the cytotoxic activity of the transduced T cells are assayed according to the method described by Yang, Z. Z. et al. (Attenuation of CD8(+) T cell function by CD4(+)CD25(+)regulatory T cells in B-cell non-Hodgkin's lymphoma, 2006, Cancer Res.) against a relevant target cell line in the presence or absence of Tregs.

The assay shows that regulatory T cells usually have an inhibitory effect on the cytotoxic capacity of CAR+ T cells, whereas p60 peptide expression by the T cell restores cytotoxic activity by lifting this inhibition.

TABLE 1

Sequences used in the examples

| Polypeptide | Amino acid sequence | SEQ ID NO # |
|---|---|---|
| p60 | RDFQSFRKMWPFFAM | SEQ ID NO: 1 |
| control (scrambled p60) | MKMFFDAFPQRRSWF | SEQ ID NO: 9 |
| linker | GSSSS | SEQ ID NO: 10 |
| Chicken lysozyme signal peptide (CLSP) | MRSLLILVLCFLPLAALG | SEQ ID NO: 11 |
| 3R CLSP | MRRRSLLILVLCFLPLAALG | SEQ ID NO: 12 |
| 4R CLSP | MRRRRSLLILVLCFLPLAALG | SEQ ID NO: 13 |
| Human lysozyme signal peptide (HSLP) | MKALIVLGLVLLSVTVQG | SEQ ID NO: 14 |
| Human interleukin 2 signal peptide (IL2SP) | MYRMQLLSCIALSLALVTNS | SEQ ID NO: 15 |
| 3K HLSP | MKKKALIVLGLVLLSVTVQG | SEQ ID NO: 16 |
| 3R IL2SP | MYRRRMQLLSCIALSLALVTNS | SEQ ID NO: 17 |

LIST OF REFERENCES CITED IN THE DESCRIPTION

Aandahl, E. M. et al. (2004) "Human CD4+ CD25+ regulatory T cells control T-cell responses to human immunodeficiency virus and cytomegalovirus antigens." *J Virol* 78: 2454-9.

Ashwell, J. D. and R. D. Klusner (1990). "Genetic and mutational analysis of the T-cell antigen receptor." *Annu Rev Immunol* 8: 139-67.

Bierer B. E. et al. (1993) "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Cabrera R. et al. (2004) "An immunomodulatory role for CD4(+)CD25(+) regulatory T lymphocytes in hepatitis C virus infection." *Hepatology* 40: 1062-71.

Cambier, J. C. (1995). "Antigen and Fc receptor signaling. The awesome power of the immunoreceptor tyrosine-based activation motif (ITAM)." *J Immunol* 155(7): 3281-5.

Casares N. et al. (2010) "A peptide inhibitor of FoxP3 impairs regulatory T cell activity and imporves vaccine efficacy in mice." *J Immunol* 185(9):5150-9.

Cooper, L. J. N. (2003). "T-cell clones can be rendered specific for CD19: toward the selective augmentation of the graft-versus-B-lineage leukemia effect". *Blood* 101 (4):1637-1644.

Cooper, Jena et al. (2012) "Good T cells for bad B cells". *Blood.* 119 (12): 2700-2702.

Cong, L., F. A. Ran, et al. (2013). "Multiplex genome engineering using CRISPR/Cas systems." *Science* 339 (6121): 819-23.

Deltcheva, E., K. Chylinski, et al. (2011). "CRISPR RNA maturation by trans-encoded small RNA and host factor RNase III." *Nature* 471(7340): 602-7.

Gasiunas, G. et al. (2012). "Cas9-crRNA ribonucleoprotein complex mediates specific DNA cleavage for adaptive immunity in bacteria." *Proc Natl Acad Sci USA* 109(39): E2579-86.

Hendersen D. J. et al. (1991) "Comparison of the effects of FK-506, cyclosporin A and rapamycin on IL-2 production." *Immun.* 73(3): 316-321.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Liu L. et al. (1991). "Calcineurin is a common target of cyclophilin-cyclosporin A and FKBP-FK506 complexes." *Cell* 66(4): 807-15.

Mali, P., L. Yang, et al. (2013). "RNA-guided human genome engineering via Cas9." *Science* 339(6121): 823-6.

Metzger, H., G. Alcaraz, et al. (1986). "The receptor with high affinity for immunoglobulin E." *Annu Rev Immunol* 4: 419-70.

Moscou, M. J. and A. J. Bogdanove (2009). "A simple cipher governs DNA recognition by TAL effectors." *Science* 326(5959): 1501.

Nicholson, I. C. (1997) "Construction and characterisation of a functional CD19 specific single chain Fv fragment for immunotherapy of B lineage leukaemia and lymphoma". *Molecular Immunology* 34(16):1157-1165.

Park T. S., S. A. Rosenberg, et al. (2011). "Treating cancer with genetically engineered T cells." *Trends Biotechnol* 29(11): 550-7.

Stoddard, B. L. (2005). "Homing endonuclease structure and function." *Q Rev Biophys* 38(1): 49-95.

Urnov F. D. et al. (2010) "Genome editing with engineered zinc finger nucleases" *Nature reviews Genetics* 11:636-646)

Viguier M. et al. (2004) "Foxp3 expressing CD4+ CD25 (high) regulatory T cells are overrepresented in human metastatic melanoma lymph nodes and inhibit the function of infiltrating T cells." *J Immunol.* 173: 1444-53.

Woo E. Y. Et al. (2001) "Regulatory CD4(+) CD25(+) T cells in tumors from patients with early-stage non-small cell lung cancer and late-stage ovarian cancer." *Cancer Res.* 61: 4766-72.

The invention claimed is:

1. A method of treating cancer in a patient in need thereof, comprising administering to the patient a therapeutically effective amount of an engineered T-cell comprising:
   a) a first exogenous nucleic acid molecule comprising a nucleotide sequence coding for a first chimeric antigen receptor (CAR) comprising an extracellular domain capable of binding to at least one antigen expressed at the surface of a malignant cell; and
   b) at least a second exogenous nucleic acid molecule comprising a nucleotide sequence coding for a peptide-inhibitor of FoxP3 comprising the amino acid sequence of SEQ ID NO 1 or SEQ ID NO:3,
   wherein the peptide-inhibitor of FoxP3 inhibits regulatory T-cell activity.

2. The method according to claim 1, wherein the engineered T-cell further comprises an exogenous nucleic acid molecule comprising a nucleotide sequence coding for a rare-cutting endonuclease that selectively inactivates a gene coding for at least one component of the T-Cell receptor (TCR).

3. The method according to claim 2, wherein the at least one component of the TCR is TCR alpha or TCR beta.

4. The method according to claim 1, wherein the inhibitor of FoxP3 is a cell penetrating peptide.

5. The method according to claim 1, wherein the first CAR and the peptide inhibitor of FoxP3 are expressed by the T-cell.

6. The method according to claim 1, further comprising a third exogenous nucleic acid molecule comprising nucleotide sequence coding for a second CAR comprising an extracellular domain capable of binding to at least one other antigen expressed at the surface of a regulatory T-cell.

7. The method according to claim 6, wherein the second CAR is expressed by the T-cell.

8. The method according to claim 1 wherein the cell further comprises a deletion or mutation in at least one gene coding for one component of the TCR.

9. The method according to claim 1, wherein the cell comprises an inactivated CD25.

10. The method according to claim 1, wherein the first CAR is directed against B-lymphocyte antigen CD19.

11. The method according to claim 6, wherein the first CAR is a single chain CAR.

12. The method according to claim 6, wherein the first and second CARs are single chain CARs.

13. The method according to claim 6, wherein the first and second CARs are multi-chain CARs.

14. The method according to claim 6, wherein the second CAR is mono-specific or multi-specific.

15. The method according to claim 6, wherein the second CAR is directed to CD25.

16. The method according to claim 1, wherein the cell is derived from a cytotoxic T-lymphocyte.

* * * * *